United States Patent
Dewdney et al.

(10) Patent No.: US 7,535,231 B2
(45) Date of Patent: May 19, 2009

(54) METHOD FOR ADJUSTMENT OF A SHIM DEVICE OF A MAGNETIC RESONANCE APPARATUS

(75) Inventors: Andrew Dewdney, Neunkirchen am Brand (DE); Sabrina Harter, Erlangen (DE); Franz Schmitt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/871,201

(22) Filed: Oct. 12, 2007

(65) Prior Publication Data
US 2008/0088306 A1    Apr. 17, 2008

(30) Foreign Application Priority Data
Oct. 12, 2006    (DE) .................. 10 2006 048 425

(51) Int. Cl.
*G01V 3/00* (2006.01)

(52) U.S. Cl. ...................... 324/320; 324/319

(58) Field of Classification Search ............... 324/320, 324/319, 318
See application file for complete search history.

(56) References Cited

U.S. PATENT DOCUMENTS

| | | | |
|---|---|---|---|
| 5,391,990 A | 2/1995 | Schmitt et al. | |
| 6,294,972 B1 * | 9/2001 | Jesmanowicz et al. | 335/301 |
| 6,687,526 B2 | 2/2004 | Brand et al. | |
| 7,235,971 B2 * | 6/2007 | Foxall et al. | 324/307 |

* cited by examiner

*Primary Examiner*—Louis M Arana
(74) *Attorney, Agent, or Firm*—Schiff Hardin LLP

(57) ABSTRACT

In a method for adjustment of a shim device of a magnetic resonance apparatus before an image acquisition in a body region that has a volume of interest, a field distribution is measured in a region encompassing the volume of interest produced with a shim device set according to a basic shim data set. A shim data set that is optimized for the volume of interest is determined by a control device starting from the basic shim data set, dependent on the field distribution; and the optimized shim data set is used for adjustment of the shim device. The basic shim data set is selected from a databank of body region-specific input shim data sets.

24 Claims, 3 Drawing Sheets

FIG 2

| Selection parameter | | | Input shim data sets |
|---|---|---|---|
| Region | Geometry | Person | |
| Head* | P1, P2 | P3, P4 | ESDS 1 |
| | P5, P6 | P7, P8 | ESDS 2 |
| | ⋮ | ⋮ | ⋮ |
| Abdomen* | P9, P10 | P11, P12 | ESDS n |
| | ⋮ | ⋮ | ⋮ |
| ⋮ | | | |

METHOD FOR ADJUSTMENT OF A SHIM DEVICE OF A MAGNETIC RESONANCE APPARATUS

BACKGROUND OF THE INVENTION

1. Field of the Invention

The present invention concerns a method for adjustment of a shim device of a magnetic resonance apparatus before an image acquisition in a body region having a volume of interest, wherein a field distribution is measured in an area encompassing the volume of interest produced with a shim device adjusted according to a basic shim data set and wherein a shim data set optimized for the volume of interest is determined by a control device dependent on the field distribution, starting from the basic shim data set and the optimized shim data set is used for adjustment of the shim device.

2. Description of the Prior Art

For image acquisition in magnetic resonance apparatuses, the homogeneity of the magnetic field in the region of interest is of great importance. Small deviations of the homogeneity can lead to large deviations of the frequency distribution, such that qualitatively substandard images are acquired.

Shim devices are known in order to improve the homogeneity in volumes of interest for an image acquisition. When a magnetic resonance apparatus is installed at its installation site, fields or field sources present in the environment can limit the built-in homogeneity of the magnetic field, in particular around the isocenter. Upon installation and start-up of a magnetic resonance apparatus, the shim device is therefore set (frequently in connection with measurements) such that as optimal a homogeneity as possible is established.

However, the subject from whom image data are to be acquired represents a further inhomogeneity source. When a person to be examined is introduced into the magnetic resonance apparatus, the matter of the body disrupts the homogeneity again. In order to counter this problem, it is known to use readjustable shim devices. In particular, electrical shim coils are known that, controlled with various shim currents, generate various compensation magnetic fields in order to improve the homogeneity.

In order to shim these disruptions of the subject to be examined, given activation of the shim device with the basic shim data set acquired during the installation and start-up of the magnetic resonance apparatus it is typical to first conduct a measurement of the field distribution using the magnetic resonance apparatus itself when the person to be examined was introduced into the patient admission of the magnetic resonance apparatus. Starting from the basic shim data set, an optimized shim data set is determined by a control device dependent on the measured field distribution. Using this optimized shim data set the shim device is then controlled in order to achieve a homogeneity as optimal as possible. Various algorithms are known to determine this optimized shim data set, but certain problems occur in the known methods.

Under some circumstances the employed algorithms do not converge at an optimized shim setting when the values of the basic shim data set are too far removed from the optimal possible values. A further error source is in the measurement of the field distribution since greater inhomogeneities, just like measurement errors, can easily lead to the situation that the algorithm supplies no optimal results.

In the prior art it is known to effect one or more further iterations, meaning to possibly effect further field measurements and to newly apply the algorithm until a user is of the opinion that the last determined shim parameter set is optimal.

For this purpose, it is known to implement a further iteration, meaning to effect a further field measurement and to apply the algorithm again until the user is of the opinion that the optimum is reached. This process is, however, extremely time-consuming and prone to error.

SUMMARY OF THE INVENTION

An object of the invention is to provide a method with which an optimal shim data set can be determined and applied in a faster and more reliable manner.

This object is achieved in accordance with the invention by a method of the aforementioned type wherein the basic shim data set is selected from a databank of body region-specific input shim data sets.

The primary problem of the conventional method lies in that the basic shim data set is based on the measurements mode during the installation of the magnetic resonance apparatus. Introduction of a body into the patient acceptance opening of the apparatus leads in part to greater inhomogeneities, such that the algorithm for optimization selects a poor starting point and does not always satisfactorily converge, or may even diverge. The inventive method provides a number of input shim data sets, organized according to various body regions, that are stored in a databank. Depending on the body region in which the image acquisition should ensue, one of the input shim data sets is then selected as a basic data set that then offers an improved starting point for the following determination of the optimized shim data set. Since the selected basic shim data set already lies much closer to the optimal shim data set to be determined, a better and faster convergence as well as a lower tendency toward error is achieved.

In the inventive method a basic shim data set is initially selected from the databank dependent on the body region to be acquired, whereupon the shim device is correspondingly controlled. As is known, the measurement of the field distribution ensues then and the algorithm determines the optimized shim data set for the volume of interest with the selected basic shim data set as a base. It should be noted that the volume of interest can be the entire body region, but can also be only a sub-volume of this body region. In both cases a differently optimized shim data set is typically determined since the homogeneity must be optimized only in a partial area in a sub-volume.

The term "body region" as used herein can encompass both a rough breakdown of the human body (head, chest area, abdominal region, leg, arm) as well as a subdivision into smaller body regions such as, for example, organs (liver, heart etc.).

Two possibilities are conceivable for determination of the input shim data sets. The input shim data sets are preferably based on measurements, and results with various persons can ideally be statistically evaluated so that a good starting point for the occurring optimization is provided. Theoretical calculations are another possibility for determination of the input shim data sets. The two determination methods naturally can be combined.

The selection of an input shim data set as a basic shim data set can ensue using a selection parameter defining the region. The control device thus receives information (the selection parameter) that specifies the body region in which the next image acquisition to be implemented should ensue. Since the input shim data sets are region-specific, an input shim data set thus can be selected from the databank as a basic shim data set.

It is also possible for further selection parameters to be considered in the selection of the basic shim data set. The input shim data sets are then differentiated not only specific to the body region but also for further selection parameters, such that a selection of an even more suitable basic shim data set can ensue by adherence to these further criteria. The convergence is thereby further increased and the tendency toward error is further reduced.

Geometric selection parameters, in particular the position and/or size and/or orientation of the region or of an organ situated in the region, can also be used as further selection parameters. If the body region or the volume of interest is not located exactly in the isocenter, this can be taken into account regarding the position. A body inclined (thus oriented) in a different way can also result in different inhomogeneities and therefore can be taken into account. This likewise applies for the size of the body region or an organ, in particular an organ that defines or contains the volume of interest. With particular advantage, the geometric selection parameters can be determined (in particular automatically) based on an overview exposure that has occurred for positioning a person to be acquired. Internal or external body surfaces are frequently recognizable in the overview exposures, from which conclusions can be made about the orientation, size and position of specific body regions. Since such overview image exposures (for example scout exposures or localizers) are frequently produced anyway, in the inventive method they can advantageously serve for (in particular automatic) determination of the geometric selection parameters. A combination of the inventive method with an automatic positioning system is possible in an embodiment. An automatic positioning system produces an overview exposure and then positions the body of the person to be acquired such that the volume of interest is located in an optimal orientation at a position optimal for the acquisition. The data of the positioning system automatically processing the overview exposure then can be taken into account for determination of the geometric selection parameters. Due to the effected settings, for example the movement of the patient bed or the tilting thereof, together with the information acquired from the overview image it is known how the body region and/or the organ are positioned and oriented and how large they are.

Additionally or alternatively, person-specific parameters (in particular the gender and/or the age and/or the weight) of a person to be acquired can be taken into account as further selection parameters. For example, different inhomogeneities occur for a child than for an adult and different inhomogeneities occur for a man than for a woman. The weight can also be a relevant selection criterion. The person-specific selection parameters can appropriately be determined from an electronic patient record. Naturally it is also possible for the data to be stored in a computer associated with the magnetic resonance apparatus. In each case the person-specific selection parameters can also be determined (in particular automatically) in this manner.

In addition to the aforementioned automatic determination of the selection parameters, it is naturally also possible for the selection parameter or selection parameters to be input at least in part by a user. For this purpose an input device can be provided with which, for example, a monitor is associated on which a corresponding input mask is displayed. It is also possible for a representation of the body (in particular an overview exposure) to be displayed to a user in which the user can, for example, mark the body region and the volume of interest. From the marking of a volume of interest, the body region surrounding it can also be concluded. A selection of the body region using, for example, clickable icons is also conceivable.

For further optimization of the shim settings it is also possible for a new measurement of a field distribution and a new determination of a new optimized shim data set to ensue as a further optimization step using the optimized shim data set as a new basic shim data set. This can also be further iterated; meaning that a number of further such optimization steps can ensue. Where applicable it is then possible to further improve the shim data sets that are already optimized to a certain extent.

In addition to the method, the invention also concerns a magnetic resonance apparatus having a basic field magnet for generation of a magnetic field in a patient receptacle, a shim device for homogenization of the magnetic field in a volume of interest from which data are to be acquired, and a control device that is fashioned for determination of an optimized shim data set from a basic shim data set and of a field distribution measured for a shim device that is set according to the basic shim data set, as well as for controlling the shim device according to a shim data set. A databank of input shim data sets specific to the body region is stored in the control device, from which databank a basic shim data set can be selected using a selection parameter defining a body region encompassing the volume of interest and possibly using at least one further selection parameter. The magnetic resonance apparatus is in particular fashioned for implementation of the inventive method.

The databank is stored in the control device, possibly in a storage device accessible by said control device. The control device can select a suitable basic shim data set from the input shim data sets based on at least one selection parameter. In the case of multiple selection parameters at least one selection parameter defines the body region encompassing the volume of interest.

The magnetic resonance apparatus can have an input device with an associated display device (in particular a monitor) allowing input of at least one selection parameter. For example, representations (in particular icons) associated with the regions can be displayed on the display device. These representations can be selected through the input device to provide the selection parameter. Alternatively, it is possible for an image representation of the body (in particular an overview exposure) to be shown on the monitor, using which image representation the selection of the body region ensues for provision of the selection parameter via the input device. Further selection parameters can be entered via such an input device, in particular geometric selection parameters such as the position and/or the size and/or the orientation of the body region or of an organ situated in the body region.

The control device can be fashioned for determination of further geometric selection parameters (in particular reflecting the position and/or size and/or orientation of the body region or of an organ situated in the body region) from an overview exposure. The image processing features necessary for this purpose are known in the prior art.

In a further embodiment, the magnetic resonance apparatus can have an automatic positioning system fashioned for optimal positioning of a body region to be acquired based on an overview exposure. The control device is fashioned for determination of at least one selection parameter from data transmitted from the positioning system. The volume of interest that should ultimately be acquired is thereby positioned by the automatic positioning system in a region of optimal homogeneity, so the homogeneity is then further improved by the inventive method and the adaptation of the shim settings. For this purpose a user must merely specify the body region and/or the volume of interest in the body region, whereupon the remaining geometric selection parameters can be determined automatically.

The control device can also communicate with a computer in which an electronic patient record is stored to determine further person-specific selection parameters, in particular the gender and/or the age and/or the weight of the person to be acquired. Such person-specific selection parameters can also be entered via the input device, for example by display of a mask on the display device.

BRIEF DESCRIPTION OF THE DRAWINGS

FIG. 2 schematically illustrates the basic structure of the databank.

DESCRIPTION OF THE PREFERRED EMBODIMENTS

Figure 1:
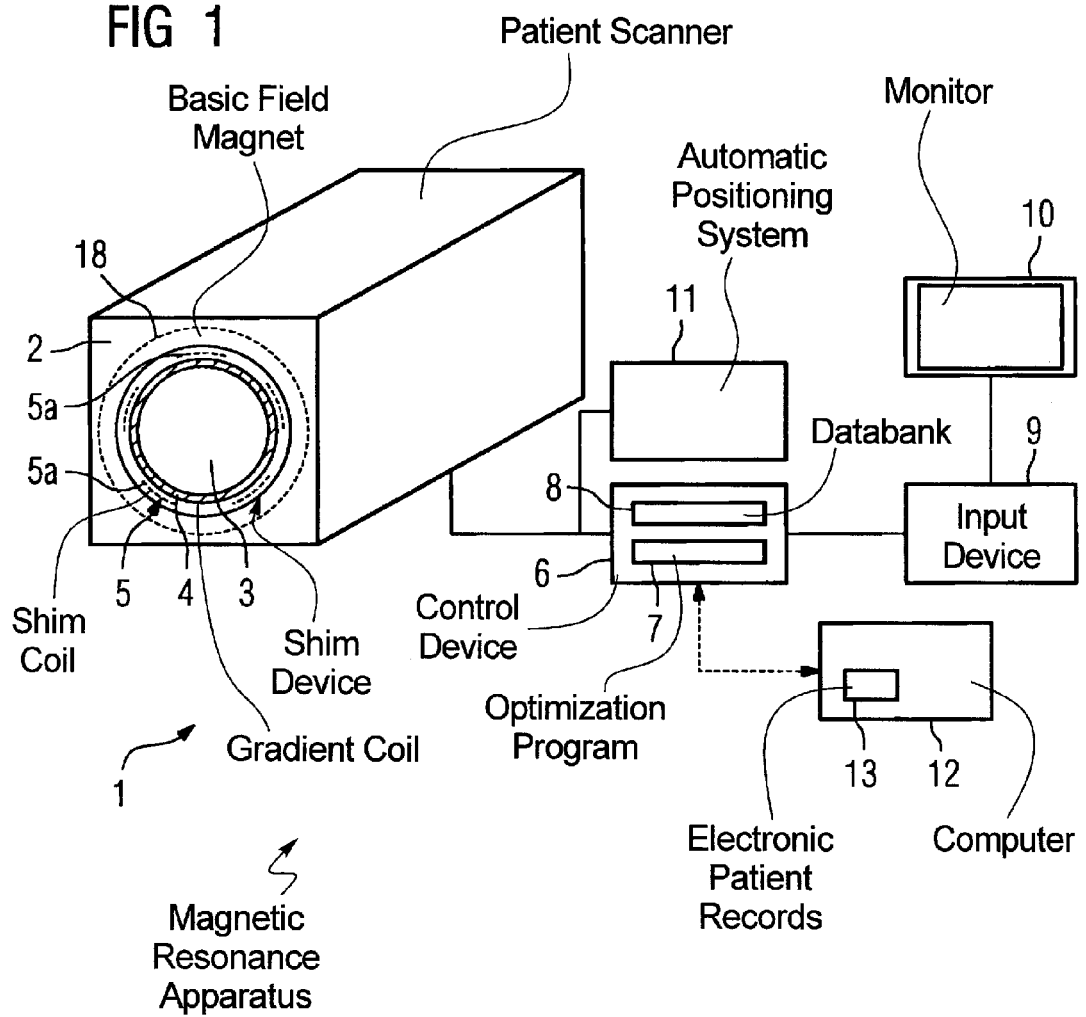
FIG. 1 schematically illustrates the basic components of an inventive magnetic resonance apparatus.

FIG. 1 shows an inventive magnetic resonance apparatus 1. The apparatus 1 has patient scanner 2 in which the basic field magnet 18 (indicated with dashed lines) is accommodated and that defines a patient receptacle 3. The patient scanner 2 has at least one gradient coil 4 with which a gradient field is generated that serves in a known manner for the spatial resolution (encoding) of the acquired measurement signals. A shim device 5 that has a number of shim coils 5a (indicated with dashed lines) that can be individually fed with current is also arranged between the gradient coils 4 and the basic field magnet 18 in the patient scanner 2. The shim coils 5a serve for the generation of fields that homogenize the magnetic field in the acquisition region. For example, five shim coils 5a can be provided that generate fields corresponding to the five field terms of a spherical function expansion of the second order.

The magnetic resonance apparatus 1 also has a control device 6 that serves for controlling the various components of the magnetic resonance apparatus 1, thus also of the shim device 5. The shim coils 5a of the shim device 5 can be fed with current via the control device 6 corresponding to a shim parameter set. The control device 6 is also fashioned to determine a shim data set optimized for a volume of interest to be acquired, by means of which shim data set the greatest possible homogeneity is achieved in the volume of interest, this determination being made from a basic shim data set and a field distribution measured given a shim device 5 set according to the basic shim data set. For example, this determination can ensue by execution of a program 7 stored in the control device 6. The program 7 is based on an algorithm.

In order to obtain an improved starting point for determination of the optimized shim data set, a databank 8 of input shim data sets specific to different body regions is also stored in the control device 6, from which databank 6 a basic shim data set can be selected using a selection parameter defining a body region encompassing the volume of interest, and possibly at least one further selection parameter. Depending on the body region and possible further selection parameters, the control device 6 can select one of the input shim data sets as an ideal starting point for determination of an optimized shim data set.

An input device 9 with an associated monitor 10 is also associated with the control device 6. Via this input device 9 the at least one selection parameter can be entered. An image representation of the body can be shown on the monitor 10, using which image representation the selection of the body region ensues to provide the selection parameter by means of the input device 9. For example, a previously produced overview exposure of the person to be examined can be displayed. In this overview exposure the operating personnel can establish the volume and/or the body region of interest using known means (for example a marking tool).

Alternatively or additionally, representations (in particular icons) associated with the regions can be displayed on the monitor 10, which representations can be selected to provide the selection parameter via the input device 9. This can ensue, for example, by means of a mouse, by a double click.

The magnetic resonance apparatus 1 also has an automatic positioning system 11 with which the volume of interest or, respectively, the selected body region can be brought into an ideal position for an acquisition. The positioning system 11 is here designated as an independent component, but it can also be integrated into the control device 6. For suitable positioning of the person to be acquired and/or of components of the magnetic resonance apparatus 1, the positioning system 11 is fashioned for evaluation of a previously produced overview exposure (frequently also called a scout exposure). The contours of a body or of organs and thus their position and orientation as well as their size can be established from such an overview exposure with known techniques. The body and possibly also components of the magnetic resonance apparatus 1 can then be moved into a position ideal for the exposure (in particular into the isocenter), for example via a corresponding activation of the patient bed.

A possibility for evaluation of such an overview exposure with regard to the size, position and/or orientation of a body region or of an organ comprised in the body region can also be provided in the control device 6.

In both cases it is possible to use such geometric information as further geometric selection parameters since these can be determined without problems from the control device 6 and/or from the positioning system 11. Naturally it is also possible that geometric parameters can be input by an operating personnel via the input device 9.

The control device 6 also communicates with a computer 12 that can be provided both externally and internally and contains electronic patient records 13. Not only can the volume of interest and the body region be determined from the knowledge of which patient should be examined, for example, but also it is also possible to determine further person-specific selection parameters, for example the gender, the age and/or the weight of the person to be acquired. Naturally it is also possible for such person-specific selection parameters to be entered via a corresponding input mask with the input device 9 and the associated monitor 10.

The basic design and the further functions as well as the mode of operation of a magnetic resonance apparatus 1 are known to those skilled in the art and need no further explanation.

FIG. 2 shows a basic representation of the design of the databank 8 that is stored in the control device 6. A number of input shim data sets 14 are respectively associated with one of multiple parameter sets 15. For clearer presentation, differentiation is made between a selection parameter defining the region, geometry-specific selection parameters and person-specific selection parameters. The star 16 indicates that the corresponding line is selected as a "default setting" given an insufficient number of known selection parameters.

The body region can be the head, the abdominal region, the chest region or an extremity, for example, however also a concrete organ (for example the liver). The geometry-specific selection parameters ultimately indicate where the body region is located, how it is oriented and which size it exhibits. The person-specific selection parameters can be the gender, the age (child/adult), the weight and further person-specific specifications. However, it is to be emphasized that the further selection parameters (in this example thus the geometry-specific and the person-specific selection parameters) are not absolutely necessary for the fundamental function of the inventive magnetic resonance apparatus and the inventive method. Just a differentiation of the input shim data sets 14 according to the body region also already allows a significant improvement of the convergence of the algorithm in the program means 7 and the speed of the calculation since a basic shim data set can be selected that already describes the inhomogeneities of the magnetic field typically caused by the body region. An adaptation must accordingly only be implemented with regard to individual properties of the person to be examined.

The input shim data sets 14 can be obtained in various ways. For example, measurement series are conceivable in which ideal shim values are determined for various persons (possibly broken down according to geometry-specific and person-specific features) and subsequently be statistically evaluated. Furthermore, it is also possible to determine the input shim data sets 14 based on theoretical calculations. A combination of both methods is also conceivable.

Figure 3:
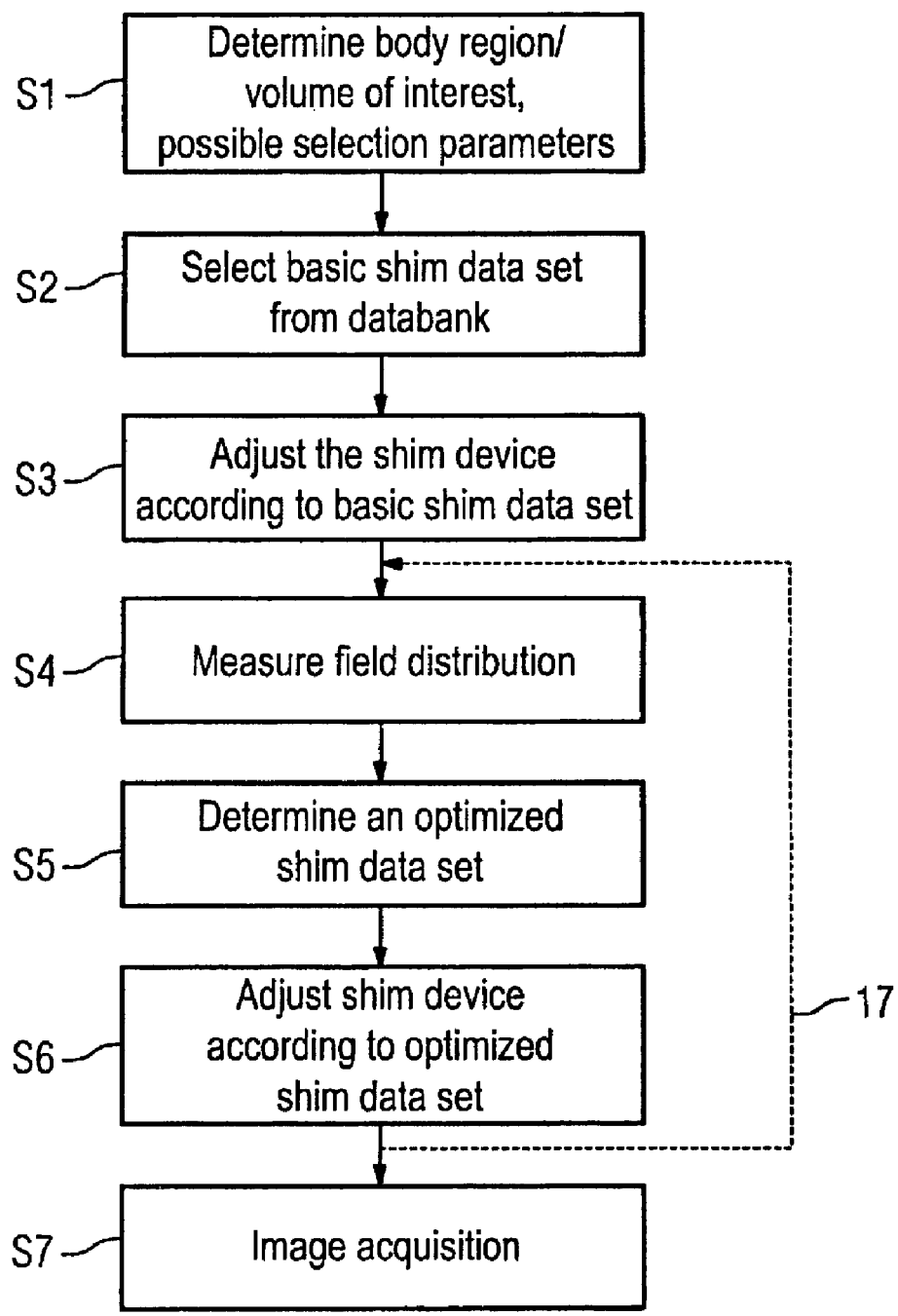
FIG. 3 is a flowchart of an embodiment of the inventive method.

FIG. 3 shows an exemplary flowchart of the inventive method. In step S1 the body region in which lies the volume of interest that should be acquired as well as the volume of interest itself is initially determined, for example via input by an operating personnel or from a patient record. The patient can now also be suitably positioned, in particular such that target volumes are located in the isocenter of the magnetic resonance apparatus 1. The positioning system 11 can be used for this. Because the selection parameter that defines the body region thus already exists, if applicable it is also possible at this point in time that further selection parameters are determined, for example person-specific selection parameters via input into a screen mask or from an electronic patient record or geometric selection parameters in the event that such are already known to the user. Further selection parameters can also be determined from an overview exposure by means of the control device 6 or from the data of the automatic positioning system 11. This has already been described in detail above.

At this point it is noted that the overview acquisition can in principle ensue at various points of the inventive method. For example, it is thus conceivable that the overview exposure is already produced at the beginning of the inventive method given the shim settings determined with the installation of the magnetic resonance apparatus 1. This is possible since these frequently concern whole-body acquisitions in which quite low requirements for the quality exist since only fundamental structures of the human body must be detected. However, it is also conceivable that initially only the selection parameters defining the body region and possibly person-specific selection parameters exist; a basic shim data set is selected under consideration of this at least one selection parameter from the databank 8; the shim device 5 is correspondingly adjusted; the overview exposure is subsequently produced and evaluated; and a further basic shim data set that is more suitable is selected from the databank 8 by means of the geometric selection parameters gained from the overview exposure.

The selection of a basic shim data set from the input shim data sets of the databank 8 then ensues in step S2. This occurs using the selection parameters determined in step S1.

In step S3 the shim device 5 is then adjusted according to the basic shim data set determined in step S2.

The measurement of the field distribution then ensues in step S4. A comparison measurement is hereby frequently implemented by means of the magnetic resonance apparatus 1, from which comparison measurement a direct conclusion is possible about the inhomogeneities of the magnetic field in the body region and in particular in the volume of interest.

A shim data set optimized for the target volume of interest is then determined in step S5 on the basis of the measured field distribution. This is the shim data set in which optimally few inhomogeneities exist. The selected basic shim data set that offers the ideal starting point for the corresponding algorithm is selected as a starting point, such that a fast and certain convergence is enabled.

The adjustment of the shim device 5 according to the optimized shim data set determined in step S5 then ensues in step S6. The image acquisition can then ensue in the following step S7.

It should be noted that the determination of the optimized shim data set in step S5 does not necessarily already lead to the optimal results after one execution of the corresponding algorithm. Multiple iterations may occur. As indicated by the dashed line 17, a one-time or multiple repetition of the steps S4-S6 can then ensue, with the optimized shim data set forms the new basic shim data set in each iteration.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for adjusting a shim device of a magnetic resonance apparatus before acquiring magnetic resonance data from the body region comprising a volume of interest, comprising the steps of:

selecting a shim data set from among a plurality of body region-specific input shim data sets stored in a data bank;

setting the shim device according to the selected body region-specific input shim data set and measuring a field distribution in the region of interest with the shim device set according to the selected body region-specific input shim data set;

in a control device, automatically optimizing said body region-specific input shim data set for said volume of interest dependent on the measured field distribution, thereby obtaining an optimized shim data set; and setting said shim device according to said optimized shim data set to produce an optimally set shim data device.

2. A method as claimed in claim 1 comprising storing shim data sets in said data bank, as said plurality of body region-specific input shim data sets, selected from the group consisting of shim data sets based on measurements and shim data sets based on theoretical calculations.

3. A method as claimed in claim 1 comprising selecting said body region-specific input shim data set using a selection parameter that defines said body region comprising the volume of interest.

4. A method as claimed in claim 3 comprising selecting said body region-specific input shim data set using further selection parameters in addition to said selection parameter defining said body region.

5. A method as claimed in claim 4 comprising using selection parameters, as said further selection parameters, selected from the group consisting of geometric selection parameters defining at least one of a position, size and orientation of said body region, and geometric selection parameters defining at least one of a position, size and orientation of an anatomical organ situated in said body region.

6. A method as claimed in claim 5 comprising generating an overview exposure of a subject containing said body region and positioning the subject in the magnetic resonance apparatus using said overview exposure, and also using said overview exposure to select said geometric selection parameters.

7. A method as claimed in claim 6 comprising positioning said patient in said magnetic resonance apparatus using an automatic positioning system that processes said overview exposure to obtain positioning system data, and using said positioning system data for selecting said geometric selection parameters.

8. A method as claimed in claim 4 comprising using patient-specific parameters, for a patient having said body region, as said further selection parameters.

9. A method as claimed in claim 8 comprising acquiring said patient-specific parameters from an electronic patient record for said patient.

10. A method as claimed in claim 3 comprising manually entering said selection parameter into said control unit by a user.

11. A method as claimed in claim 1 comprising repeating measurement of said field distribution with said shim device set according to said optimized shim data set and, in said control device, automatically further optimizing said optimized data set dependent on said field distribution, to obtain a more optimized shim data set.

12. A method as claimed in claim 11 comprising, in said control device, automatically executing multiple iterations of field distribution measurement and shim set optimization using, in each iteration, the more optimized shim data set from an immediately preceding iteration.

13. A magnetic resonance apparatus comprising:
a patient scanner configured to receive a patient therein, said patient having a body region comprising a volume of interest;
a basic field magnet in said patient scanner that generates a basic magnetic field in which said body region is located;
a shim device in said patient scanner that operates according to a shim data set to homogenize said basic magnetic field in said volume of interest;
a magnetic field detector that measures a field distribution of a field in said volume of interest that is a combination of said basic magnetic field and a field generated by said shim device;
selecting a basic shim data set from among a plurality of body region-specific input shim data sets stored in a data bank;
a data bank in which a plurality of body region-specific input shim data sets are stored;
a control unit that selects one of the body region-specific input shim data sets from the data bank and that sets the shim device according to the selected body region-specific input shim data set, and measures a field distribution in the region of interest with the shim device set according to the selected body region-specific input shim data set;
said control unit automatically optimizing said body region-specific input shim data set for said volume of interest dependent on the measured field distribution, thereby obtaining an optimized shim data set; and
said control unit setting said shim device according to said optimized shim data set to produce an optimally set shim data device.

14. An apparatus as claimed in claim 13 wherein said data bank, as said plurality of body region-specific input shim data sets stored therein, stores data sets selected from the group consisting of shim data sets based on measurements and shim data sets based on theoretical calculations.

15. An apparatus as claimed in claim 13 wherein said control unit selects said body region-specific input shim data set using a selection parameter that defines said body region comprising the volume of interest.

16. An apparatus as claimed in claim 15 wherein said control unit selects said body region-specific input shim data set using further selection parameters in addition to said selection parameter defining said body region.

17. An apparatus as claimed in claim 16 wherein said control unit uses selection parameters, as said further selection parameters, selected from the group consisting of geometric selection parameters defining at least one of a position, size and orientation of said body region, and geometric selection parameters defining at least one of a position, size and orientation of an anatomical organ situated in said body region.

18. An apparatus as claimed in claim 17 wherein said control unit operates said patient scanner to generate an overview exposure of a subject containing said body region and operates a patient table to position the subject in the magnetic resonance apparatus using said overview exposure, and also uses said overview exposure to select said geometric selection parameters.

19. An apparatus as claimed in claim 18 comprising an automatic positioning system that processes said overview exposure to obtain positioning system data for positioning said patient in said magnetic resonance apparatus, and wherein said control unit uses said positioning system data to select said geometric selection parameters.

20. An apparatus as claimed in claim 16 wherein said control unit uses patient-specific parameters, for a patient having said body region, as said further selection parameters.

21. An apparatus as claimed in claim 20 wherein said control unit acquires said patient-specific parameters from an electronic patient record for said patient.

22. An apparatus as claimed in claim 15 comprising an input unit allowing manual entry of said selection parameter into said control unit by a user.

23. An apparatus as claimed in claim 13 wherein said control unit repeats measurement of said field distribution with said shim device set according to said optimized shim data set, and automatically further optimizes said optimized data set dependent on said field distribution, to obtain a more optimized shim data set.

24. An apparatus as claimed in claim 23 wherein said control unit automatically executes multiple iterations of field distribution measurement and shim set optimization using, in each iteration, the more optimized shim data set from an immediately preceding iteration.

* * * * *